United States Patent [19]

Spangler, deceased

[11] 4,133,893

[45] Jan. 9, 1979

[54] TOPICAL TREATMENT OF SKIN DISEASES

[75] Inventor: Arthur S. Spangler, deceased, late of Weston, Mass., by Barbara F. Spangler, executrix

[73] Assignee: Calbiochem Behring Corp., La Jolla, Calif.

[21] Appl. No.: 800,807

[22] Filed: May 26, 1977

[51] Int. Cl.² ............................................. A61K 31/03
[52] U.S. Cl. ................................................. 424/354
[58] Field of Search ........................................ 424/354

[56] References Cited
U.S. PATENT DOCUMENTS 4,061,753  12/1977  Bodor et al. ..................... 424/253

OTHER PUBLICATIONS

Molnar et al., Cancer, vol. 16, pp. 259–268 (1963).
Helson et al., Clinical Chemistry, vol. 17, No. 12, pp. 1191–1193 (1971).
Kupfer et al., Federation Proceedings, vol. 35, No. 13, pp. 2603–2608 (1976).
Chemical Abstracts 76:121407r (1972).
Physicians Desk Reference (PDR), 26th Ed., pp. 809–811 (1972).

Primary Examiner—Leonard Schenkman
Attorney, Agent, or Firm—Natalie Jensen

[57] ABSTRACT

A topical preparation for the treatment of skin diseases such as acne vulgaris, acne rosacea, psoriasis and herpes simplex which comprises 1,1-dichloro-2-(o-chlorophenyl)-2-(p-chlorophenyl)ethane and a pharmaceutically acceptable carrier or diluent.

2 Claims, No Drawings

TOPICAL TREATMENT OF SKIN DISEASES

The present invention relates to a pharmaceutical composition for treating diseases of the skin. More particularly, the invention relates to a topical preparation comprising 1,1-dichloro-2-(o-chlorophenyl)-2-(p-chlorophenyl)ethane and a pharmaceutically acceptable carrier or diluent.

Skin diseases which are not only unsightly but which can also be very painful affect a large segment of the population. Acne vulgaris, for example, which is a chronic skin disease affecting the sebaceous glands of various parts of the body, is one of the most common conditions seen by dermatologists. The principal clinical manifestation of the disease is the occurrence of numerous cutaneous lesions which involve the pilosebaceous follicles on the face, shoulders, chest and back. Acne rosacea, also a chronic skin disease frequently seen by dermatologists, is a condition which affects the nose, forehead and cheeks. This disease is marked by flushing of the aforementioned areas followed by capillary dilatation with the appearance of papules and acne-like pustules.

Another chronic skin disease is psoriasis. The clinical manifestation of the disease is a distinctive lesion, i.e., a vivid red papule which is covered by silvery lamellated scales. This disease generally appears for the first time in adolescence or early adult life.

Still another skin disease which can affect the appearance and which is frequently painful is herpes simplex. The condition is marked by groups of vesicles on the skin, often on the borders of the lips or the nares, or on the genitals.

All of the aforementioned skin diseases are persistent and difficult to treat. Despite numerous treatments advocated in the prior art for these and other skin diseases, the fact is that very few work. Such treatments have included not only various topical preparations but also systemic regimens such as the use of steroids and antibiotics. Concern about the possible side effects of long-term systemic use of steroids and antibiotics only emphasizes the long-felt need for a safe and effective topical preparation.

Accordingly, it is the primary object of the present invention to provide a safe and effective topical pharmaceutical composition for the treatment of skin diseases.

It is a further object of the present invention to provide a pharmaceutical composition which may be readily prepared and which may be used as a topical treatment for skin diseases such as acne vulgaris, acne rosacea, psoriasis and herpes simplex.

These and other objects and advantages of the instant invention will become apparent upon consideration of the following disclosure and claims.

It has been unexpectedly found that compositions containing 1,1-dichloro-2-(o-chlorophenyl)-2-(p-chlorophenyl)ethane may be effectively used to topically treat various skin diseases including acne vulgaris, acne rosacea, psoriasis and herpes simplex.

Although 1,1-dichloro-2-(o-chlorophenyl)-2-(p-chlorophenyl)ethane has been reported as being useful in the treatment of adrenocortical carcinoma, it has heretofore never been reported as being a suitable agent for the topical treatment of skin diseases.

Accordingly, the present invention is directed to a pharmaceutical composition for treating skin diseases such as acne vulgaris, acne rosacea, psoriasis and herpes simplex which composition comprises an effective amount of 1,1-dichloro-2-(o-chlorophenyl)-2-(p-chlorophenyl)ethane and a pharmaceutically acceptable carrier or diluent.

Suitable vehicles for topical application of 1,1-dichloro-2-(o-chlorophenyl)-2-(p-chlorophenyl)ethane to the skin are well known in the art and include various liquids, gels, creams, ointments, lotions, solutions, suspensions and the like. Pharmaceutically acceptable carriers or diluents which may be used according to the instant invention include, for example, alcohols such as methanol, ethanol, propanol, isopropanol and mixtures thereof; water-alcohol solutions; and polyalkylene glycol solutions, e.g., alcoholic solutions of polyethylene glycol or polypropylene glycol. Pharmaceutical excipients which may also be present in the compositions of the present invention include, for example, cellulose, starch and the like. Preferred pharmaceutical compositions for topical application comprise 1,1-dichloro-2-(o-chlorophenyl)-2-(p-chlorophenyl)ethane in 95-100% alcohol. Ethanol or isopropanol being preferred.

The concentration of 1,1-dichloro-2-(o-chlorophenyl)-2-(p-chlorophenyl)ethane in pharmaceutical compositions suitable for topical application will vary depending upon the condition and subject being treated. In general, topical preparations containing 0.1 to 30% by weight of 1,1-dichloro-2-(o-chlorophenyl)-2-(p-chlorophenyl)ethane are advantageously employed. Compositions containing 1 to 12% by weight, 1,1-dichloro-2-(o-chlorophenyl)-2-(p-chlorophenyl)ethane are preferred. The composition is usually applied about 1-6 times daily in the conventional amounts, that is, amounts sufficient to cover affected areas. The treatment is continued until or after all manifestations of the skin disease have disappeared.

The following examples of formulations which have been employed in the treatment of skin diseases such as acne vulgaris, acne rosacea, psoriasis and herpes simplex are given to enable those skilled in the art to more clearly understand the invention. The examples should not be considered as a limitation upon the scope of the invention but merely as being illustrative and representative thereof. It should be noted that the formulation percentages recited hereinafter (e.g., 10% cream, 12.5% lotion) refer to weight/volume percentages.

EXAMPLE 1

10% cream

The formulation comprises the following ingredients:

| | |
|---|---|
| 1,1-dichloro-2-(o-chlorophenyl)-2-(p-chlorophenyl)ethane | 20.0 g. |
| Distilled water | 50.0 ml. |
| Aquaphor (a mixture of wool wax, mineral wax, white petrolatum and white oil) | 130.0 g. |

Water was added to 1,1-dichloro-2-(o-chlorophenyl)-2-(p-chlorophenyl) ethane to make a paste, and the paste was then incorporated into the Aquaphor ointment and well levigated.

25% cream was prepared according to the above procedure by using 50 g. of 1,1-dichloro-2-(o-chlorophenyl)-2-(p-chlorophenyl)ethane.

EXAMPLE 2

10% lotion

The formulation comprises the following ingredients:

| | |
|---|---|
| 1,1-dichloro-2-(o-chlorophenyl)-2-(p-chlorophenyl)ethane | 150.0 g. |
| Ethanol (70%) (V/V) | 1050.0 ml. |
| Calamine lotion* q.s. | 1500.0 ml. |

*A pharmaceutical preparation comprising zinc oxide and about 0.5% ferric oxide.

The alcohol was added to 1,1-dichloro-2-(o-chlorophenyl)-2-(p-chlorophenyl)ethane with vigorous mixing. Calamine lotion was then added to the mixture to obtain a volume of 1500 ml.

EXAMPLE 3

12.5% lotion
The formulation comprises the following ingredients:

| | |
|---|---|
| 1,1-dichloro-2-(o-chlorophenyl)-2-(p-chlorophenyl)ethane | 180.0 g. |
| Ethanol (50%) (V/V) | 720.0 ml. |
| Propylene glycol q.s. | 1440.0 ml. |

1,1-dichloro-2-(o-chlorophenyl)-2-(p-chlorophenyl)ethane was macerated with 400 ml. of the alcohol. After 30 minutes the suspension was filtered. The precipitate was washed with the balance of alcohol (320 ml.) and the mixture filtered. Propylene glycol was then added to the combined filtrates with agitation and the resultant lotion was well mixed.

EXAMPLE 4

A. 20% lotion
The formulation comprises the following ingredients:

| | |
|---|---|
| 1,1-dichloro-2-(o-chlorophenyl)-2-(p-chlorophenyl)ethane | 288.0 g. |
| Ethanol (50%) (V/V) | 720.0 ml. |
| Propylene glycol q.s. | 1440.0 ml. |

1,1-dichloro-2-(o-chlorophenyl)-2-(p-chlorophenyl)ethane was macerated with 400 ml. of the alcohol. After 30 hours the suspension was filtered. The precipitate was washed with the balance of alcohol (320 ml.) and the mixture filtered. Propylene glycol was then added to the combined filtrates with agitation and the resultant lotion was well mixed.

B. 20% lotion
The formulation comprises the following ingredients:

| | |
|---|---|
| 1,1-dichloro-2-(o-chlorophenyl)-2-(p-chlorophenyl)ethane | 144.0 g. |
| Propylene glycol | 72.0 ml. |
| Ethanol (50%) (V/V) | 720.0 ml. |

1,1-dichloro-2-(o-chlorophenyl)-2-(p-chlorophenyl)ethane was macerated with 300 ml. of the alcohol. After 4 hours the suspension was filtered. The precipitate was washed with 320 ml. of alcohol and the mixture filtered. Propylene was slowly added to the combined filtrates with agitation. Thereafter the remainder of the ethyl alcohol was added to give 720 ml. of lotion.

EXAMPLE 5

25% lotion
The formulation comprises the following ingredients:

| | |
|---|---|
| 1,1-dichloro-2-(o-chlorophenyl)-2-(p-chlorophenyl)ethane | 180.0 g. |
| Ethanol (50%) (V/V) q.s. | 720.0 ml. |

1,1-dichloro-2-(o-chlorophenyl)-2-(p-chlorophenyl)ethane was macerated with the alcohol. After 30 minutes the suspension was filtered. The precipitate was washed with alcohol and the mixture filtered. Alcohol was then added to combined filtrates to obtain a volume of 720 ml.

Clinical Example

A female patient diagnosed as having psoriasis with lesions of the legs and elbows was treated with various types of therapy over a long period of time with little or no success. She then began therapy with the 25% cream formulation of Example 1. The patient applied the cream to the left elbow only, and the lesions nearly cleared up in two weeks. Therapy on the left lower leg was conducted using six topical applications daily of the 12.5% lotion formulation of Example 3. After approximately two months the patient began applying the 20% lotion formulation of Example 4 (part B) to the left lower leg. Continued improvement of the psoriasis condition on the left lower leg was observed.

The invention being thus described, it will be obvious that the same may be varied in many ways. Such variations are not to be regarded as a departure from the spirit and scope of the invention, and all such modifications are intended to be included within the scope of the following claims.

What is claimed is:

1. A method for topically treating skin diseases selected from the group consisting of acne vulgaris, acne rosacea and herpes simplex which method comprises applying to affected areas of the skin a pharmaceutical composition comprising an effective amount of 1,1-dichloro-2-(o-chlorophenyl)-2-(p-chlorophenyl)ethane and a pharmaceutically acceptable carrier or diluent suitable for topical application.

2. A method according to claim 1 wherein said pharmaceutical composition contains from about 0.1 to 30% by weight of 1,1-dichloro-2-(o-chlorophenyl)-2-(p-chlorophenyl)ethane.

* * * * *